United States Patent
Shum et al.

(10) Patent No.: US 12,239,981 B2
(45) Date of Patent: Mar. 4, 2025

(54) AUTOMATIC MICROFLUIDIC SYSTEM FOR CONTINUOUS AND QUANTITIVE COLLECTION OF DROPLETS

(71) Applicant: THE UNIVERSITY OF HONG KONG, Hong Kong (HK)

(72) Inventors: Ho Cheung Shum, Hong Kong (HK); Lang Nan, Hong Kong (HK); Yuk Heng Tang, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 1083 days.

(21) Appl. No.: 17/251,229

(22) PCT Filed: Jul. 10, 2019

(86) PCT No.: PCT/CN2019/095408
§ 371 (c)(1),
(2) Date: Dec. 11, 2020

(87) PCT Pub. No.: WO2020/011193
PCT Pub. Date: Jan. 16, 2020

(65) Prior Publication Data
US 2021/0260587 A1 Aug. 26, 2021

Related U.S. Application Data

(60) Provisional application No. 62/696,419, filed on Jul. 11, 2018.

(51) Int. Cl.
*B01L 3/00* (2006.01)
*G01N 15/14* (2006.01)
(Continued)

(52) U.S. Cl.
CPC .... *B01L 3/502746* (2013.01); *B01L 3/502715* (2013.01); *B01L 3/502738* (2013.01);
(Continued)

(58) Field of Classification Search
CPC ......... B01L 3/502784; B01L 3/502761; B01L 3/502738; B01L 3/502746;
(Continued)

(56) References Cited

U.S. PATENT DOCUMENTS 4,756,427 A * 7/1988 Gohde ............. B01L 3/502761
209/552
5,858,195 A * 1/1999 Ramsey ............. B01L 3/50273
204/600

(Continued)

OTHER PUBLICATIONS

International Search Report and Written Opinion for International Application No. PCT/CN2019/095408 mailed on Oct. 9, 2019, 6 pages.

*Primary Examiner* — Shogo Sasaki
(74) *Attorney, Agent, or Firm* — Amin, Turocy & Watson, LLP

(57) ABSTRACT

An automatic system which combines a three-branch sorter with three independently-controlled valves and corresponding collection platforms. The subgroups of droplets are alternatively sorted into three channels followed by being pumped out into PCR tubes on the platforms. Experimentally, this system can realize an accurate collection with a large working range for both pure positive samples and mixed samples with negative ones. This technology effectively dispenses a large number of droplets into small subgroups with quantitative number, which builds the basis for digital droplet microfluidics.

8 Claims, 6 Drawing Sheets

(51) Int. Cl.
  *G01N 15/1492* (2024.01)
  *G01N 21/64* (2006.01)
  *C12M 3/06* (2006.01)
  *C12Q 1/6806* (2018.01)
  *G01N 15/149* (2024.01)

(52) U.S. Cl.
  CPC ... *B01L 3/502761* (2013.01); *B01L 3/502784* (2013.01); *G01N 15/147* (2013.01); *G01N 15/1484* (2013.01); *G01N 15/1492* (2024.01); *G01N 21/64* (2013.01); *B01L 2300/0645* (2013.01); *B01L 2300/0864* (2013.01); *B01L 2300/0874* (2013.01); *B01L 2400/0424* (2013.01); *B01L 2400/0487* (2013.01); *C12M 23/16* (2013.01); *C12Q 1/6806* (2013.01); *G01N 2015/1481* (2013.01); *G01N 15/149* (2024.01)

(58) Field of Classification Search
  CPC ....... B01L 3/502715; B01L 2300/0874; B01L 2400/084; B01L 2300/0841; B01L 2400/0424; B01L 2300/0645; B01L 2400/0487; B01L 2300/0864; G01N 15/147; G01N 15/1492; G01N 21/64; G01N 15/1484; G01N 15/149; G01N 2015/1006; G01N 2015/1481; C12M 23/16; C12Q 1/6806
  See application file for complete search history.

(56) References Cited

U.S. PATENT DOCUMENTS

| | | | | |
|---|---|---|---|---|
| 5,876,675 A * | 3/1999 | Kennedy | .......... | G01N 27/44791 356/244 |
| 6,174,675 B1 * | 1/2001 | Chow | .......... | B01L 7/52 435/6.19 |
| 6,321,791 B1 * | 11/2001 | Chow | .......... | B01L 3/502707 137/833 |
| 6,432,720 B2 * | 8/2002 | Chow | .......... | B01L 9/527 216/2 |
| 6,506,609 B1 * | 1/2003 | Wada | .......... | B01F 33/3011 422/50 |
| 6,540,895 B1 * | 4/2003 | Spence | .......... | G01N 15/14 204/600 |
| 6,577,453 B2 | 6/2003 | Kimura | | |
| 6,592,821 B1 * | 7/2003 | Wada | .......... | B01L 3/502776 435/7.1 |
| 6,632,619 B1 * | 10/2003 | Harrison | .......... | B01L 3/5027 436/805 |
| 6,778,724 B2 * | 8/2004 | Wang | .......... | H05H 3/04 428/188 |
| 6,783,647 B2 * | 8/2004 | Culbertson | .......... | C12N 1/066 204/453 |
| 6,808,075 B2 * | 10/2004 | Bohm | .......... | F15C 5/00 209/172.5 |
| 7,091,048 B2 * | 8/2006 | Parce | .......... | B01J 19/0093 436/514 |
| 7,138,269 B2 * | 11/2006 | Blankenstein | .......... | B01D 57/02 436/514 |
| 8,691,164 B2 * | 4/2014 | Butler | .......... | G01N 33/5005 422/503 |
| 8,765,485 B2 * | 7/2014 | Link | .......... | B01F 25/45 422/503 |
| 9,089,844 B2 | 7/2015 | Hiddessen et al. | | |
| 10,551,295 B2 * | 2/2020 | Bassler | .......... | G01N 21/64 |
| 11,022,537 B2 * | 6/2021 | Otsuka | .......... | G01N 15/14 |
| 2003/0159999 A1 * | 8/2003 | Oakey | .......... | B01L 3/502715 210/243 |
| 2003/0198523 A1 * | 10/2003 | Bohm | .......... | F16K 99/0048 406/198 |
| 2005/0092658 A1 * | 5/2005 | Bohm | .......... | F16K 99/0028 209/172.5 |
| 2005/0109410 A1 * | 5/2005 | Gilbert | .......... | F16K 99/0036 137/827 |
| 2005/0207940 A1 * | 9/2005 | Butler | .......... | B01L 3/502776 422/403 |
| 2007/0184489 A1 * | 8/2007 | Griffiths | .......... | B01L 3/502761 435/7.1 |
| 2008/0124726 A1 * | 5/2008 | Monforte | .......... | G01N 33/56966 435/7.1 |
| 2008/0213821 A1 * | 9/2008 | Liu | .......... | B81C 1/00444 264/483 |
| 2008/0261295 A1 * | 10/2008 | Butler | .......... | C12M 47/04 436/53 |
| 2012/0152369 A1 | 6/2012 | Hiddessen et al. | | |

* cited by examiner

AUTOMATIC MICROFLUIDIC SYSTEM FOR CONTINUOUS AND QUANTITIVE COLLECTION OF DROPLETS

TECHNICAL FIELD

Disclosed is an on-demand collection of droplets with accurate quantity, which can further realize a quantitative collection of desired targets encapsulated in droplets.

BACKGROUND

Droplets are discrete volumes of liquid generated with the use of immiscible phases. Compared with conventional reactors, droplets have mainly three advantages. Firstly, the small size, normally in the scale of picolitre to nanolitre, can largely reduce the required reaction volumes, thus increasing the whole detection and analysis efficiency. Secondly, the interface generates a natural barrier to diffusion, which can provide the encapsulated components with separated space to prevent from further contamination in subsequent operations. Thirdly, compared with directly manipulating the encapsulated components, it is easier to manipulate droplets in a larger size, thus being able to combine more detection and analysis parts together to realize integrated operations. Due to these advantages, droplets perform as ideal microcontainers for biological and chemical substances. Thus, droplet-based microfluidics, which integrate different functional models with the ability to transport, mix, split, and sort droplets, has been developed into a wide variety of areas, including cell sorting, drug discovery, and particle synthesis.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

Normally, droplets are generated at a high frequency from 10 Hz to over 100 Hz, making it difficult to accurately control droplet number to realize an on-demand collection, or divide a large group of droplets into some quantitative subgroups, especially continuous operations without the waste of samples. However, this is quite in demand in some precise applications, such as single-cell analysis to study the cellular behavior for individual cells and micro tissue engineering to coculture several different types of cells with an accurate ratio, which require quantitative control and analysis of the encapsulated targets.

Aiming at a more convenient and effective collection, this disclosure presents an automatic system to continuously dispense a certain number of droplets into arrays of Polymerase Chain Reaction (PCR) tubes. This system utilizes a fluorescence-activated three-branch droplet sorter to alternatively drive subgroups of droplets into different channels with different Dielectrophoresis (DEP) forces, followed by actuating compressed air to pump out droplets into the PCR tubes placed on three rotation platforms. The system of the present invention is capable of continuously collecting a minimum number of 30 droplets into each tube for symmetric collection. And a lower-number collection, even the single-droplet collection, can be realized in one branch channel through increasing collection numbers in other two branch channels for asymmetric collection. Furthermore, reserving one channel for waste sample and two others for alternative collection effectively combines droplet sorting with quantitative collection, being able to sort a certain number of positive droplets into each tube. In one embodiment, cancer cells were encapsulated in droplets and tested, which shows a large working range with a high accuracy.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

40, (c) 50, and (d) 100. A bright white light is used so that the outline of droplets can be clearly identified. Scale bars: 100 μm.

Figure 8:
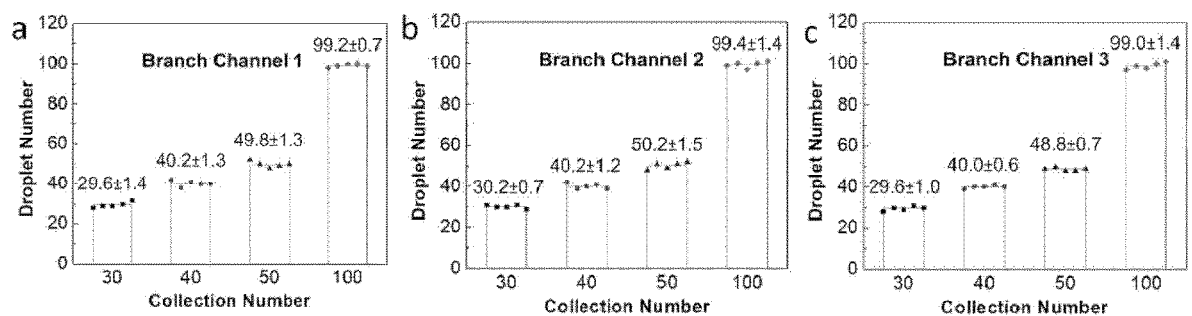

FIG. 8 reports the statistical results of droplet number in (a) branch channel 1, (b) branch channel 2, and (c) branch channel 3 for collection number of 30, 40, 50 and 100.

Figure 9:
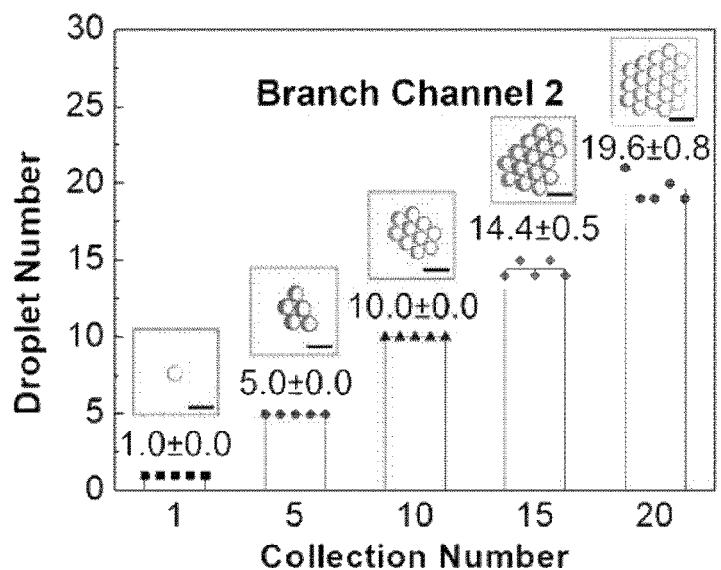

FIG. 9 reports statistical results and optical images to show the collected droplet number in branch channel 2 for asymmetric collection of 50-1-50, 50-5-50, 50-10-50, 50-15-50, and 50-20-50. Scale bars: 100 μm.

Figure 10:
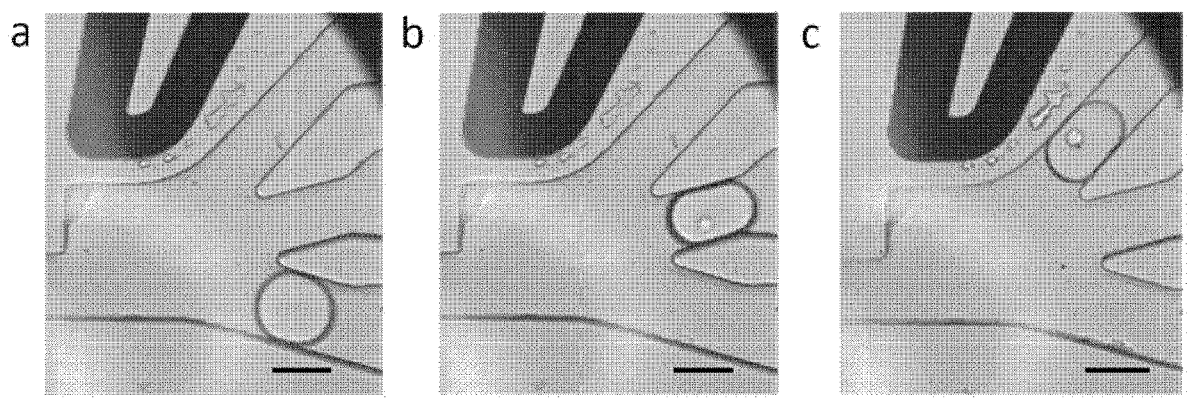

FIG. 10 provides optical images to show the alternative sorting of droplets encapsulating cells. While negative droplets sorted into (a) branch channel 1, subgroups of positive droplets are alternatively sorted into (b) branch channel 2 and (c) branch channel 3. Scale bars: 50 μm.

Figure 11:
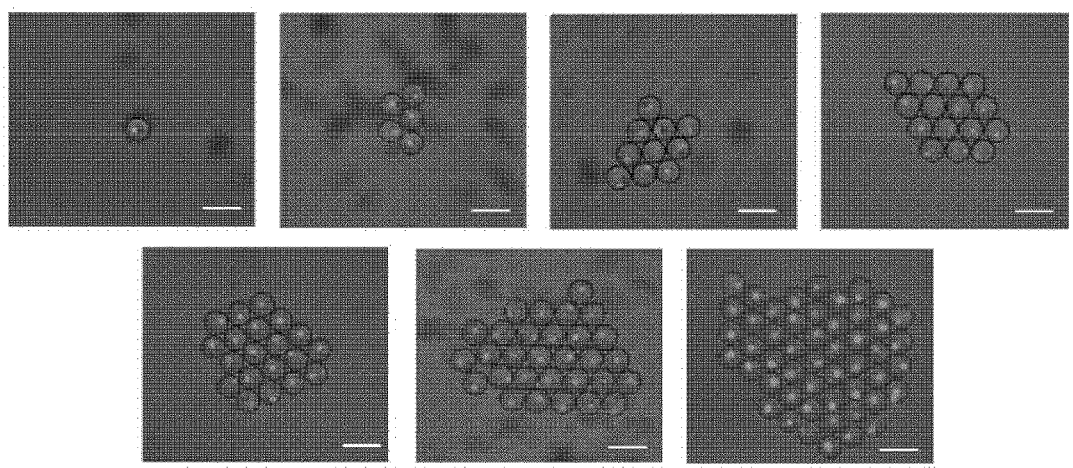

FIG. 11 provides fluorescence images of collected droplets for the collection numbers of 1, 5, 10, 15, 20, 30, and 50. Scale bars: 100 μm.

Figure 12:
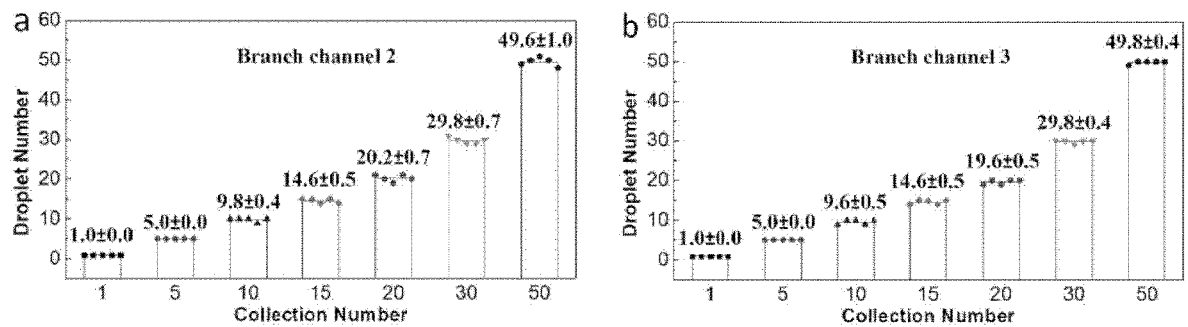

FIG. 12 reports statistical results to show the collected droplet number in (a) channel 2 and (b) branch channel 3 for different collection numbers from 1 to 50.

Figure 13:
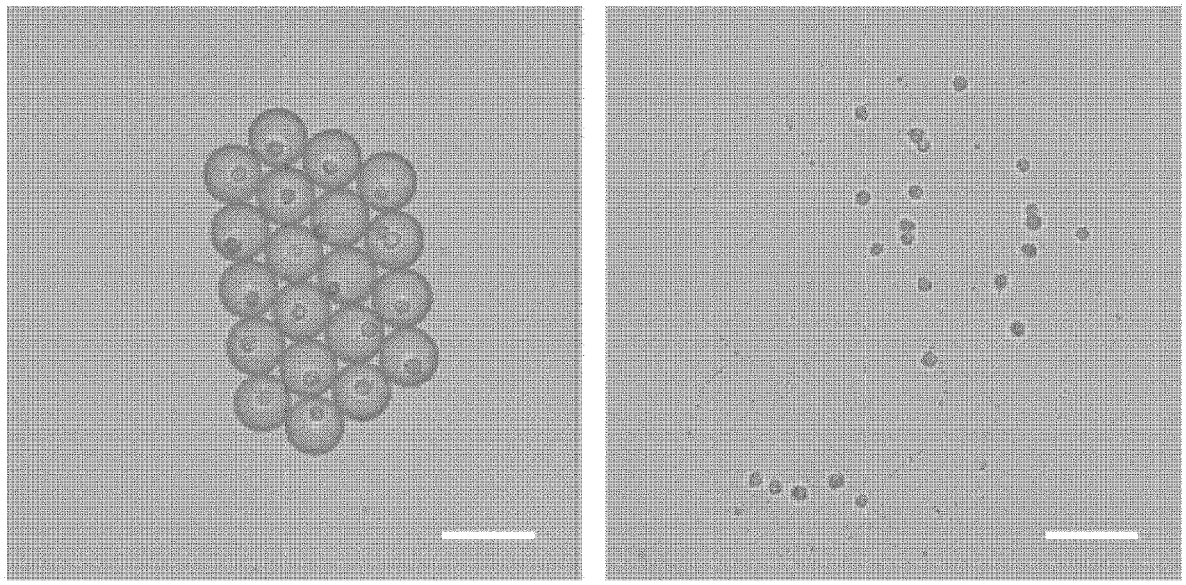

FIG. 13 demonstrates that 20 droplets containing cancer cells are accurately collected and recovered, with all 23 cells extracted. Scale bars: 100 μm.

DETAILED DESCRIPTION

The disclosure is presented in several embodiments in the following description with reference to the Figures.

Figure 1:
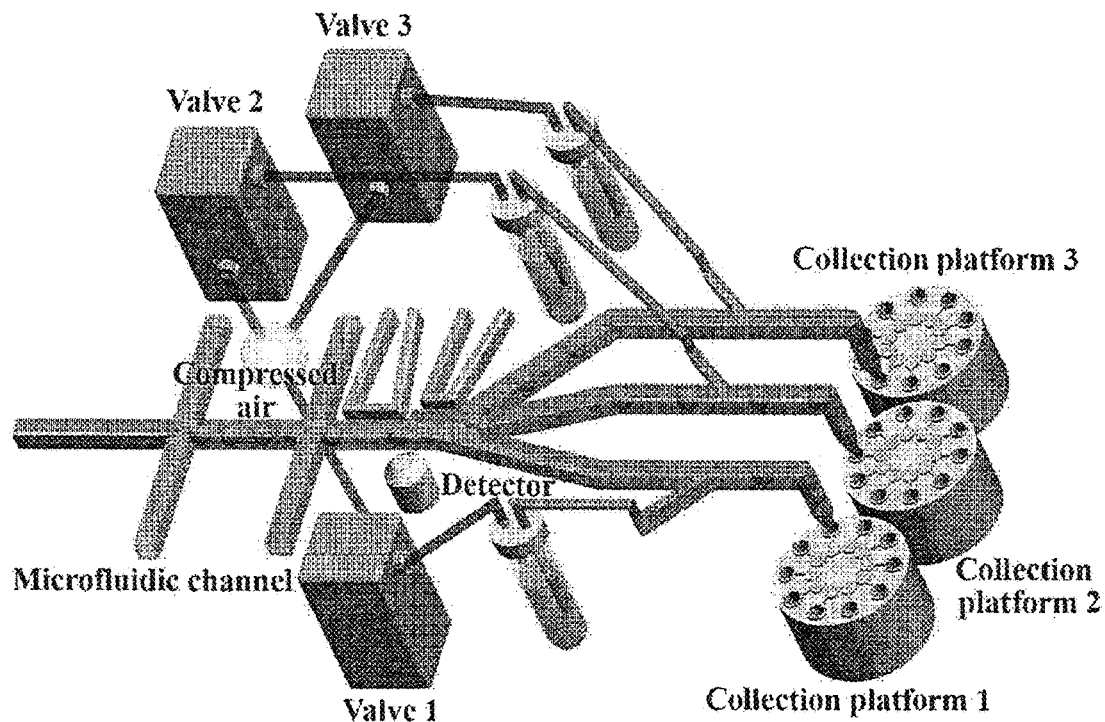
FIG. 1 depicts a schematic of the droplet collection system. Droplets are generated in the microfluidic channel and generating a triggering signal after flowing through detection area. Based on the detected signals, output sorting signal is supplied to the electrode to alternatively sort droplets into three branch channels. Then pumping oil are used to pump out droplets into rotation platforms for quantitative collection.

This collection system consists of a three-branch sorter, three independently-controlled valves and corresponding collection platforms, as shown in FIG. 1. The quantitative collection is realized through alternatively driving subgroups of droplets into three branch channels, thus leaving enough interval between adjacent subgroups going into the same channel to complete each collection. The collection process can be divided into three steps: droplet generation, three-branch sorting, and droplet collection.

Figure 2:
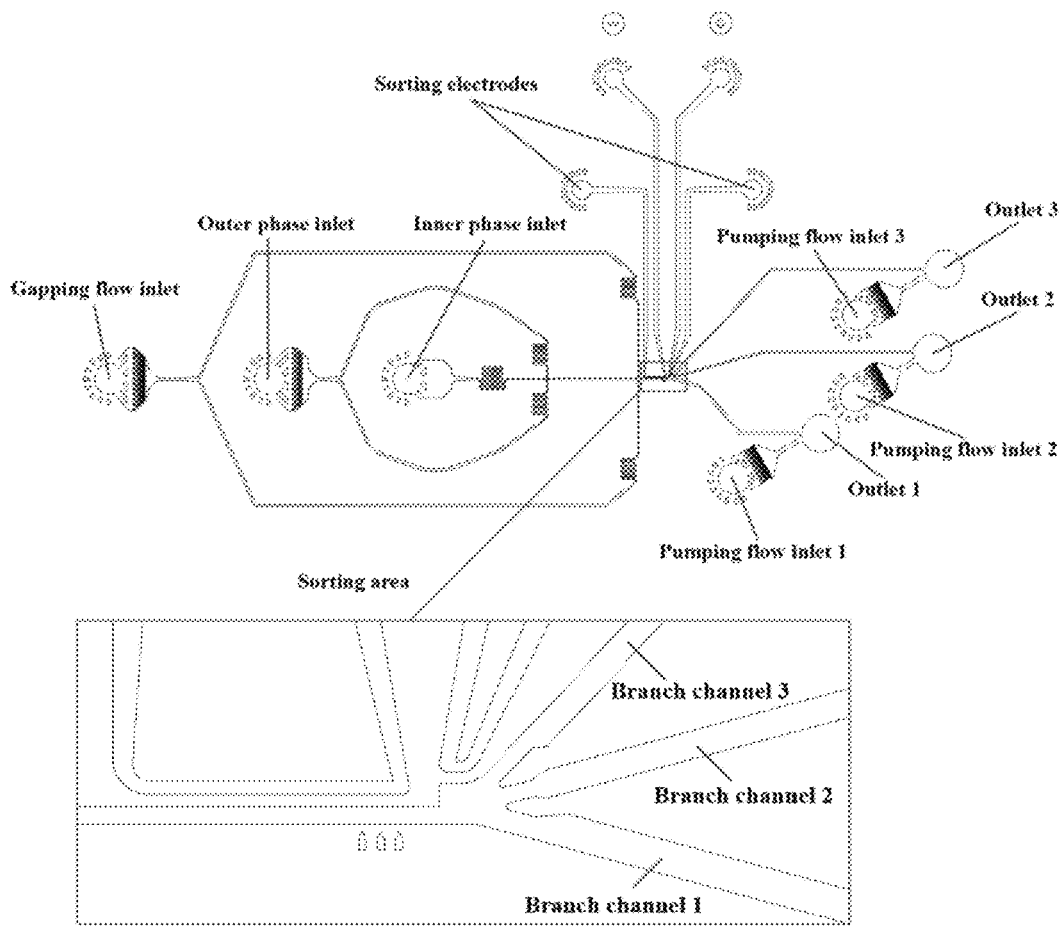
FIG. 2 depicts a design of microfluidic channel. The integrated microfluidic channel consists of one inlet for inner phase, one inlet for outer phase, and one inlet for spacing flow. Sorting electrodes are used to generate DEP field for sorting droplet into branch channels. Droplets are pumped out of outlets by introducing outer phase from pumping flow inlets.

A flow-focusing microfluidic channel was used for the generation and gapping of droplets, as shown in FIG. 2. To realize stable and accurate sorting in next step, two requirements should be met in this part: sufficiently small droplet size to prevent channel blocking, and adequate gap between adjacent droplets to complete individual sorting. Therefore, a relatively low ratio of inner phase to outer phase flow rate (normally from 1:100 to 1:30 according to different aqueous samples) was used, corresponding to the droplet diameter of around 60 μm. And a sufficiently high gapping flow rate (normally higher than 200 μL/h) is used to guarantee enough gap.

Figure 3:
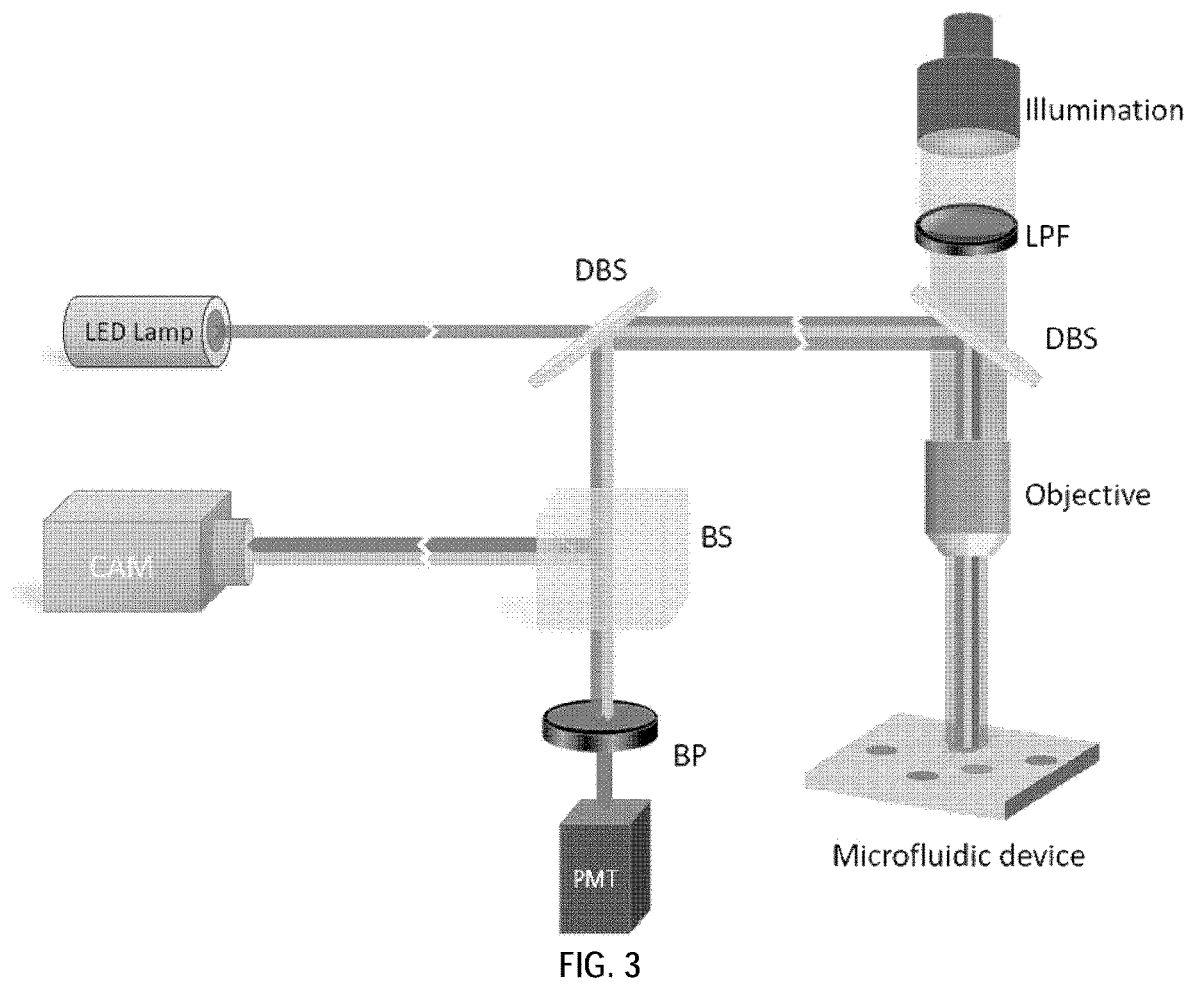
FIG. 3 depicts a sketch of the optical setup. The excitation laser (LASER) travels through the dichroic beam splitter (DBS) and is focused by an objective (OBJ) to the channel for fluorescence excitation and detection. The emitted fluorescence travels back and is filtered by a bandpass filter (BP) before collection onto a photodetector (PMT). For a simultaneous imaging process with fluorescence detection, the beam splitter (BS) splits the light of the fluorescence emission and the image illumination light into a high-speed camera (CAM) and the PMT. The illumination wavelength is filtered by a long pass filter (LP) to remove the wavelength that overlaps with the fluorescence signal from the droplets.
Figure 4:
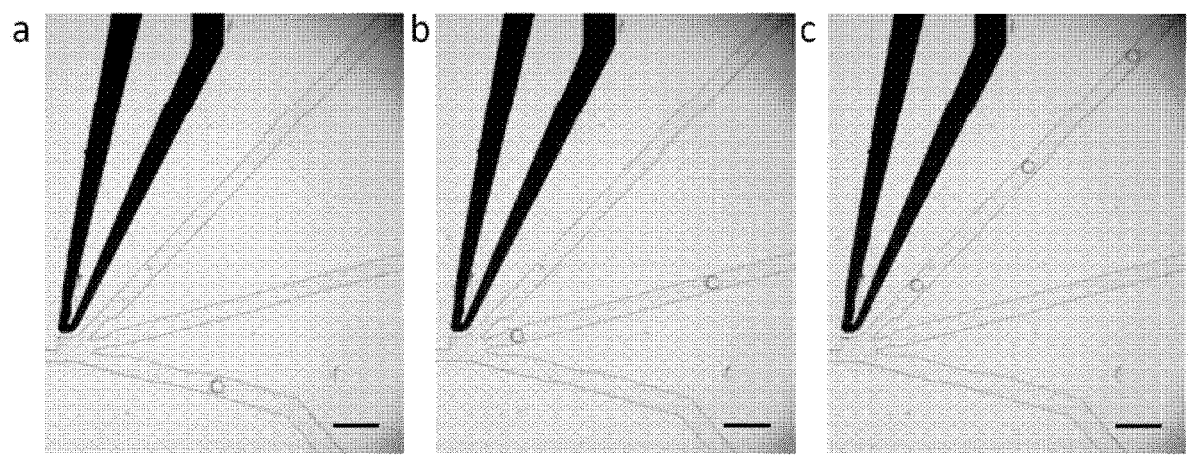
FIG. 4 illustrates that, based on different applied voltages, droplets are respectively sorted to (a) branch channel 1, (b) branch channel 2 and (c) branch channel 3. Scale bars: 200 µm.

When droplet flowed through the detection area, its arrival can be detected by an optical detector beneath the microfluidic device, which can identify the fluorescence with a wavelength of 488 nm, as shown in FIG. 3. Based on the detected signals, an automatic program edited by LabVIEW was used to process the input data at 100 kHz. And the output sorting signal was amplified by a high voltage amplifier followed by being supplied to the electrode to sort the droplets. As shown in FIG. 2, the three branch channels were designed with different fluidic resistance: channel 1 is the widest and shortest, while branch channel 3 is the narrowest and longest. Thus, droplets are supposed to choose channel 1 due to the lowest fluidic resistance. Furthermore, the three channels were designed asymmetric to the horizontal line: branch channel 1 and 2 has the same horizontal angle of 15°, while channel 3 has a larger one of 45°, resulting in the effect of inertial force being higher on branch channel 1 and 2, but lower on branch channel 3. Therefore, at normal conditions, droplets tended to flow into channel 1; while applying a lower sorting voltage of 370 Vpp with the frequency of 10 kHz, droplets were driven into branch channel 2; with a higher voltage of 650 Vpp, droplets were driven into branch channel 3, as shown in FIG. 4. In one embodiment, the lower sorting voltage is in a range of 350-450 Vpp and the higher voltage is in a range of 600-900 Vpp. Based on this, subgroups of droplets were alternatively driven into three channels for continuous collection, while negative droplets flowing into branch channel 1 and subgroups of positive droplets alternatively driven into branch channel 2 and 3 for sorting combined with collection.

Figure 5:
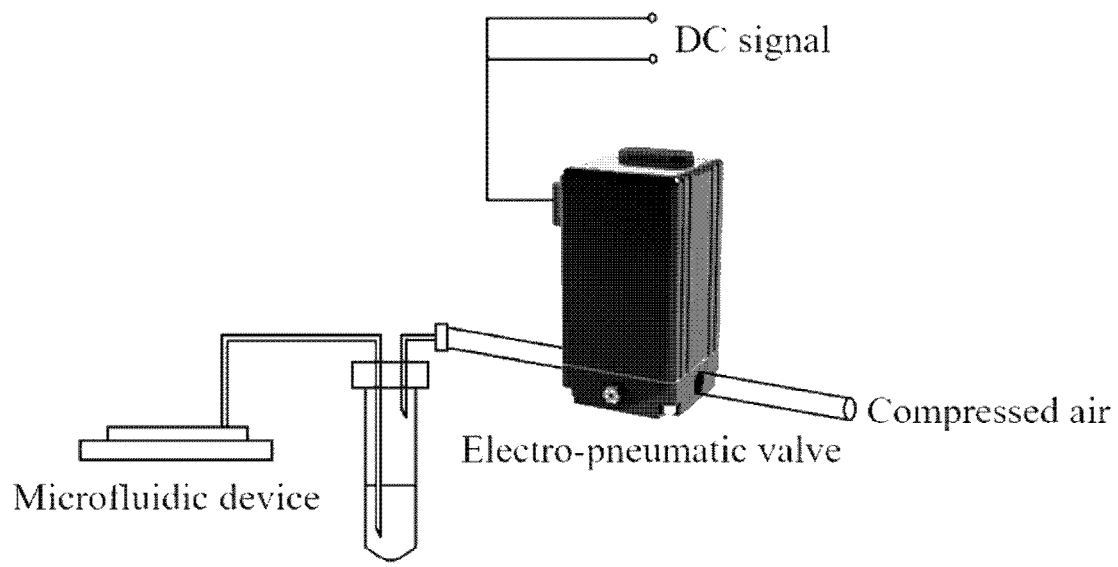
FIG. 5 depicts a schematic of electro-pneumatic valve. The valve can generate different air pressures according to different direct current (DC) voltages. After receiving an input signal, it can quickly drive the outer phase flow through compressed air to pump out the droplets.
Figure 6:
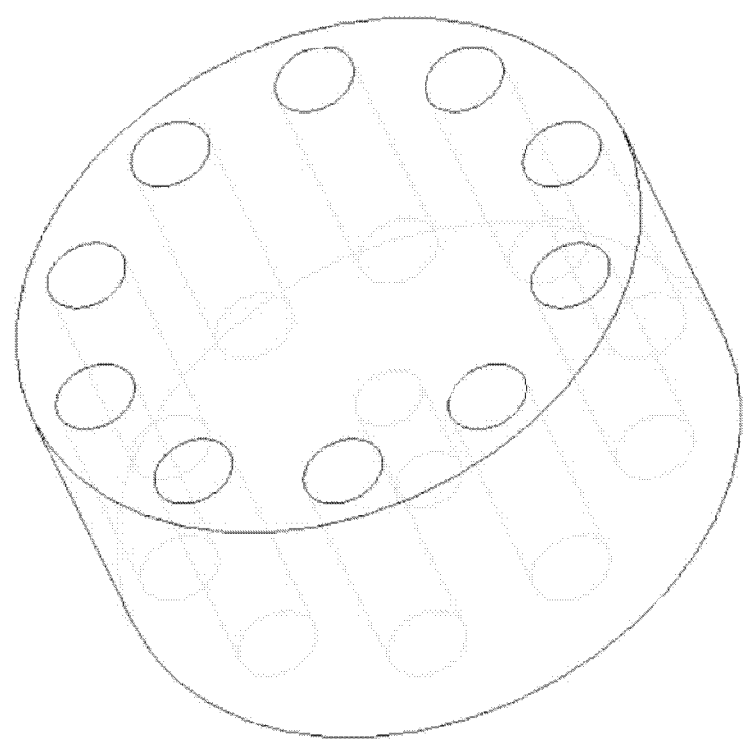
FIG. 6 depicts a design of collection platforms. The platform is fabricated with a 3D printer to collect the droplets. Ten holes on the top are used to hold the PCR tubes and a step motor is fixed on the bottom to control its rotation.

After one subgroup of droplets being sorted into corresponding channel, the connected valve (FIG. 5) and rotation platform (FIG. 6) were successively operated to complete this collection. A compressed air-driven outer phase flow was utilized to rapidly pump out droplets into the PCR tube through a curved needle. To ensure that droplets have flowed into the outlet while opening valve to start pumping, delay times of 1.5 s, 2 s and 2.5 s were applied to channel 1, 2 and 3 for valve opening, respectively. And in consideration of the fluidic perturbation caused by pumping flow, which may induce sorting instability, a DC voltage of 1.2 V was output to the valve, corresponding to the air pressure of around 8 kPa and pumping flow rate of around 12,000 μL/h. At this relatively high flow rate, the inner phase flow was temporarily stopped to avoid this instability. To guarantee droplets be completely pumped out, the pumping volume and valve open time of were set at 5 μL and 1.5 s, respectively. Finally, after another delay time of 0.5 s for the droplets to drip into the PCR tube, 20 cycles of TTL signal with the frequency of 150 Hz was output to the step motor, driving the collection platform to rotate 36° to another tube in around 0.13 s for the next subgroup collection, as shown in movie 1.

Figure 7:
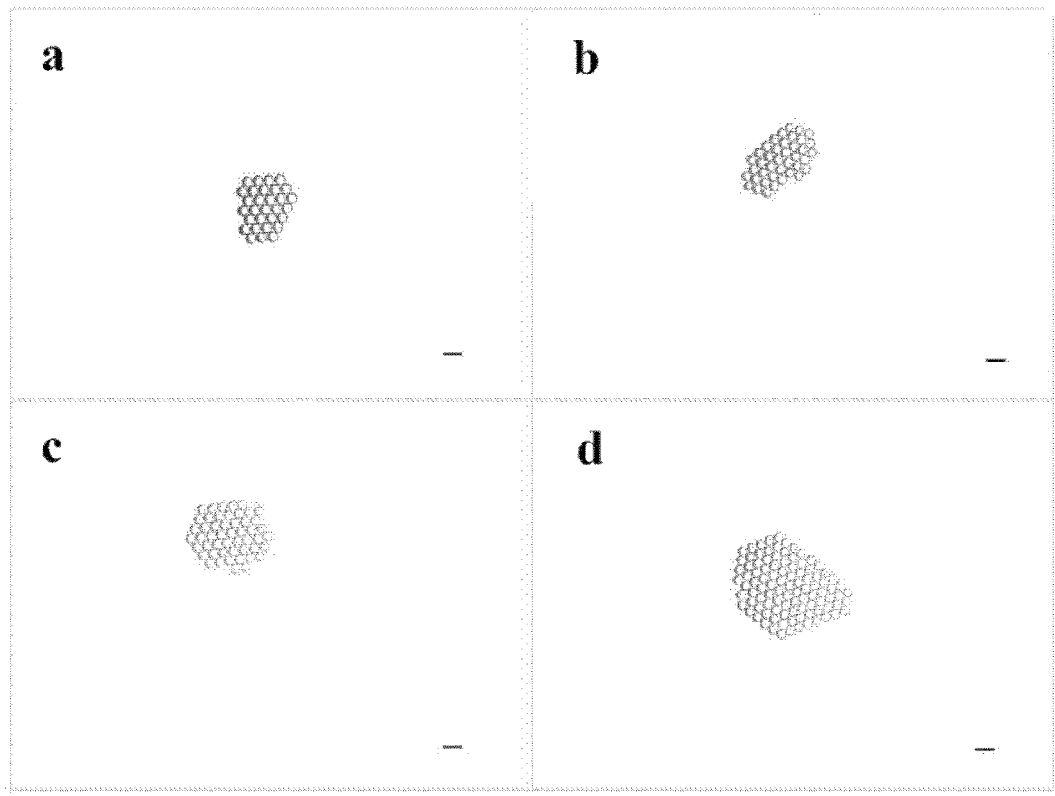
FIG. 7 provides optical images to show the collected droplet number for different collection numbers of (a) 30, (b)

To perform continuous collection of homogeneous droplets, a kind of fluorescent dye was tested as the inner phase to continuously generate and collect positive droplets. The inner phase, outer phase and gapping flow rates were set as 5 μL/h, 500 μL/h and 200 μL/h, corresponding to the droplet diameter of 54 μm and generation frequency of around 14 Hz. Firstly, a symmetric collection was tested, which means that three channels collect the same number of droplets for each subgroup. To verify the interval between adjacent subgroups going into the same channel be longer than each collection time, the collection number for each subgroup should be beyond a minimum value of 25. In one embodiment, the collection number is adjusted as a parameter in LabVIEW. Based on this, the collection number was respectively set as 30, 40, 50 and 100 to test this system. The optical images of collected droplets are shown in FIG. 7, and statistical results of droplet number are shown in FIG. 8. It can be seen from the figure that this system can accurately collect different numbers of droplets, with only a small quantitative deviation. Furthermore, if the collection numbers in two channels are increased to supply longer interval, the collection number in the other channel can be accordingly reduced, which is called asymmetric collection and can realize a low-number collection in one channel. To verify this, the collection numbers in channel 1 and 3 were both set as 50, and the number in channel 2 was set as a lower value of 20, 15, 10, 5, and 1, respectively. Experimentally, this method can accurately collect a relatively low number of droplets, and even realize the single-droplet collection, as shown in FIG. 9.

While reserving branch channel 1 for negative sample and the other two channels for alternative collection, this system can effectively combine droplet sorting with quantitative collection, thus collecting a certain number of desired droplets into each PCR tube, as shown in FIG. 10. To verify this, a kind of cancer cell (KYSE 150) with the diameter of 10-50 µm was tested for this system. The flow rates of inner phase, outer phase and gapping flow were set at 10 µL/h, 300 µL/h and 300 µL/h, respectively, corresponding to the droplet size of 66 µm and generation frequency of 18 Hz. Limited by the collection time, there is a threshold for the minimum collection number, n, which is closely related to the average number of microspheres in each droplet, A. Experimentally, while the ratio between n and A is beyond 100, a stable quantitative collection can be achieved. Based on this, the concentration of fluorescent microspheres was diluted to three different levels, corresponding to the A of 0.2, 0.05 and 0.01, and sorting frequency of around 4 Hz, 1 Hz and 0.2 Hz, respectively. To test the system, the collection numbers of 20, 30 and 50 were tested for the A of 0.2; the collection numbers of 5, 10, 15 were tested for the A of 0.05; and single positive droplet collection was tested for the A of 0.01. Fluorescence images of collected droplets are illustrated to show the droplet number and the encapsulation of cancer cells, as shown in FIG. 11. In addition, FIG. 12 illustrates the counted droplet numbers for different collection numbers, which shows a high accuracy at a large working range.

On the basis of on-demand collection of microfluidic droplets, a novel recovery method to extract the encapsulants inside the droplets was also developed. Specifically, it is completed by collecting the droplet emulsions into a culture plate filled with aqueous medium. Under the effect of interfacial tension, the oil phase will spread to a thin layer and the droplets rapidly aggregate at the center. Then as the oil layer gradually evaporates, the droplet phase will directly merge into the aqueous medium when the oil phase completely evaporates (FIG. 13). This method realizes non-invasive and lossless droplet extraction in around 20 s, allowing integration with conventional biological assays to directly analyze the target encapsulants, such as cells, microbes and genetic molecules, in aqueous phase.

Unless otherwise indicated in the following examples and elsewhere in the specification and claims, all parts and percentages are by weight, all temperatures are in degrees Centigrade, and pressure is at or near atmospheric pressure.

With respect to any figure or numerical range for a given characteristic, a figure or a parameter from one range may be combined with another figure or a parameter from a different range for the same characteristic to generate a numerical range.

Other than in the operating examples, if any, or where otherwise indicated, all numbers, values and/or expressions referring to parameters, measurements, conditions, etc., used in the specification and claims are to be understood as modified in all instances by the term "about."

While the invention is explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. An integrated system, comprising:
a microfluidic device;
a multi-branch sorter configured to receive droplets from a microfluidic channel of the microfluidic device and drive subgroups of the droplets into respective different branch channels based on a value of a sorting signal applied to one or more sorting electrodes, the multi-branch sorter comprising:
an optical detection setup comprising a diode-pumped solid state (DPSS) laser source configured to direct a fluorescence emission on a detection area of the microfluidic channel; and
a high-speed camera coupled with a beam splitter and configured to perform fluorescence detection and optical imaging of droplets that arrive at the detection area based on the fluorescence emission, wherein the fluorescence detection controls the value of the sorting signal; and
independently controlled electro-pneumatic valves connected, via tubing, to the different branch channels, respectively, wherein the electro-pneumatic valves are configured to drive compressed air into the respective different branch channels that pump the subgroups of droplets into collection platforms associated with the respective different branch channels.

2. The integrated system of claim 1, wherein
the microfluidic device comprises a main channel in which droplets are generated and gapped,
the different branch channels comprises three branch channels into which the droplets are separated into the subgroups of droplets, and
the coupled electrodes are configured to perform dielectrophoresis sorting of the subgroups of droplets into the three branch channels.

3. The integrated system of claim 1, wherein the independently controlled electro-pneumatic valves are controlled to create a time delay between respective opening times of the independently controlled electro-pneumatic valves.

4. The integrated system of claim 1, further comprising rotation collection platforms, wherein a rotation collection platform of the rotation collection platforms comprises:
a plurality of holes on a top of the rotation collection platform that are configured to hold micro polymerase Chane Reaction (PCR) tubes that receive the subgroups of droplets, and
a step motor fixed on a bottom of the rotational collection platform and configured to rotate the rotation collection platform.

5. The integrated system of claim 4, wherein the rotation collection platform comprises ten holes on the top that are configured to hold the micro PCR tubes.

6. The integrated system of claim 1, wherein the DPSS laser source is focused on the detection area through a multi-edge dichroic mirror and a plan objective.

7. The integrated system of claim 1, wherein the different branch channels comprise respective different fluidic resistances based on respective different lengths and widths of the different branch channels.

8. The integrated system of claim 6, wherein the plan objective is a plan fluorite objective.

* * * * *